United States Patent
Gazi et al.

(10) Patent No.: US 7,320,696 B2
(45) Date of Patent: Jan. 22, 2008

(54) SEMI-STATIONARY BALLOON IN THE GASTRIC ANTRUM PROVIDED WITH CONNECTING AN ANCHORING ROD FOR INDUCING WEIGHT REDUCTION IN HUMAN BEINGS

(76) Inventors: Bashir Mussa Gazi, Av. Duque De Caxias, 2-6 -Vila Mesquita-, Bauru- Sp- (BR); Paulo Sakai, Rua Evaristo De Morais, 55 Apto 71 -Vila Mariana, -São Paulo - Sp - (BR); Fabio Pinatel Lopasso, Alameda Franca, 1570 Apto 22-Jd. Paulista, -São Paulo - Sp- (BR)

( * ) Notice: Subject to any disclaimer, the term of this patent is extended or adjusted under 35 U.S.C. 154(b) by 476 days.

(21) Appl. No.: 10/872,910

(22) Filed: Jun. 21, 2004

(65) Prior Publication Data

US 2004/0267378 A1    Dec. 30, 2004

(30) Foreign Application Priority Data

Jun. 24, 2003    (BR) .................................... 0302240

(51) Int. Cl.
*A21M 29/00*    (2006.01)
(52) U.S. Cl. ..................................... 606/192
(58) Field of Classification Search ............... 606/191, 606/192, 195
See application file for complete search history.

(56) References Cited

U.S. PATENT DOCUMENTS 5,084,061 A * 1/1992 Gau et al. .................... 606/195
5,234,454 A * 8/1993 Bangs ......................... 606/191

* cited by examiner

*Primary Examiner*—Michael J. Hayes
*Assistant Examiner*—Michael G. Mendoza
(74) *Attorney, Agent, or Firm*—Notaro & Michalos P.C.

(57) ABSTRACT

A semi-stationary balloon in the gastric antrum provided with an anchoring rod for inducing weight reduction in human beings is disclosed, a device for inducing a lesser appetite and early prandial satiety, said balloon being made of inflatable per-os medical grade silicone having a volume of up to 240 ml, with an average space of 120 ml to be filled with non-elastic fluid provided with radio-opaque contrast and dye, preferably methylene blue, so that the maximum diameter of 8 cm is reached after it is filled up with a volume of up to 240 ml and the average diameter of 6 cm with a volume of 120 ml, to be endoscopically placed inside the stomach (E); said intra-gastric balloon (1) being positioned in a semi-stationary way in the gastric antrum (GAC) and provided with an anchoring or duodenal rod (2) having a distal counter-weight (5) installed in the duodenum (D); particularly, the inner face of the pear-shaped medium portion of lesser diameter is coated with a malleable ribbon (f) that provides said balloon (1) with resistance and flexibility.

9 Claims, 1 Drawing Sheet

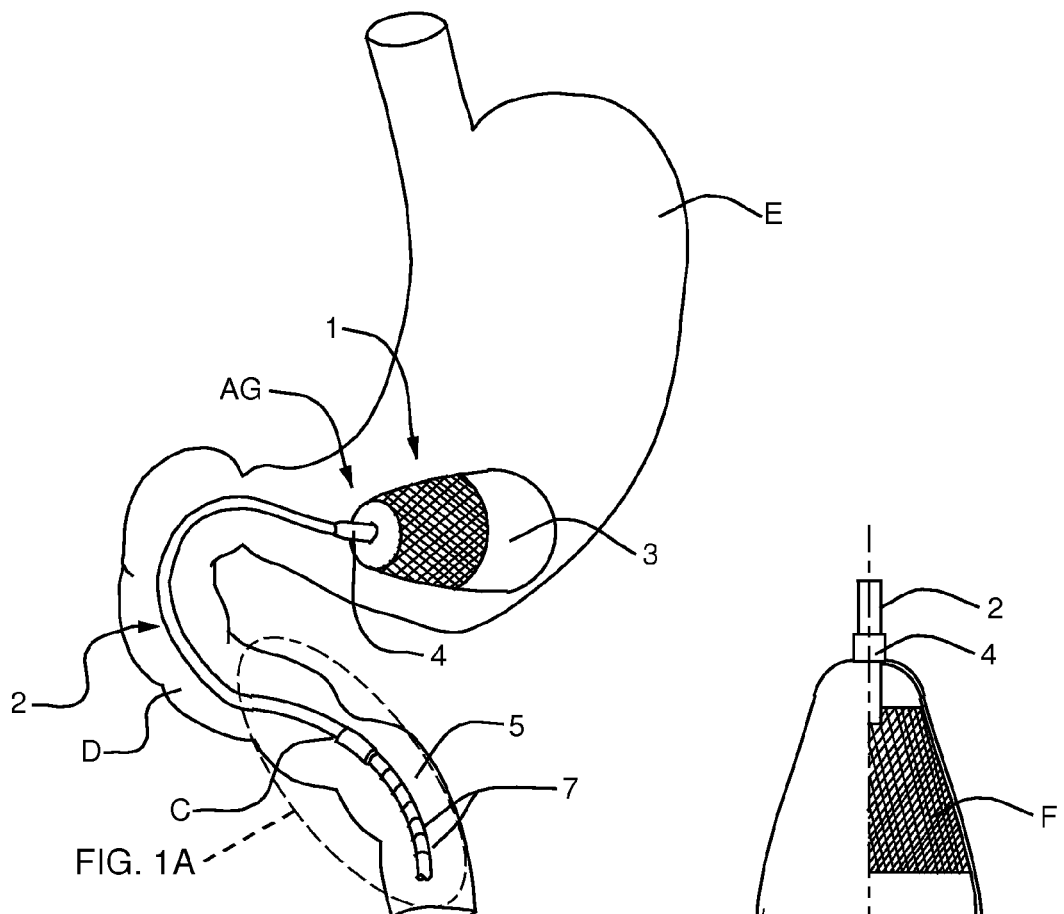
FIG. 1
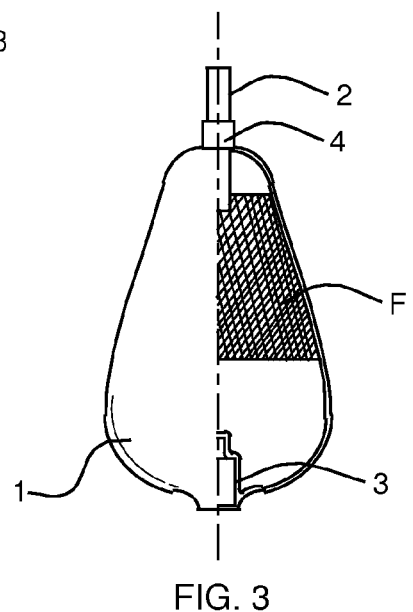
FIG. 3
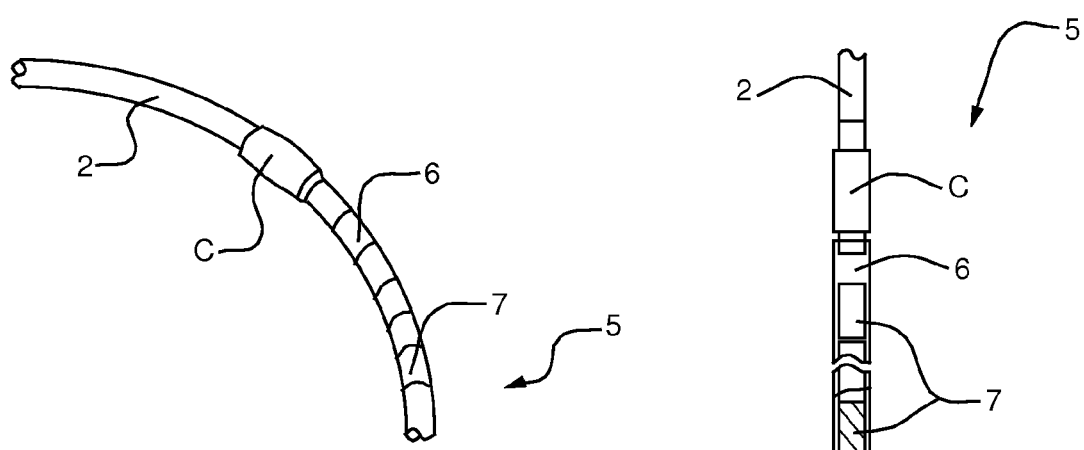
FIG. 1A
FIG. 2

SEMI-STATIONARY BALLOON IN THE GASTRIC ANTRUM PROVIDED WITH CONNECTING AN ANCHORING ROD FOR INDUCING WEIGHT REDUCTION IN HUMAN BEINGS

DISCLOSURE OF THE INVENTION

1. Technical Field

The present invention is directed to a semi-stationary balloon in the gastric antrum provided with an anchoring rod for inducing weight reduction in human beings, particularly applied as an element that occupies the gastric cavity partially, making it possible to propose an intragastric device that induces weight reduction as the gastric antrum expands and that, by being stationary in the antrum, allows for the antrum pyloric sub-occlusion, only during the response to the increase in the motor activity of the antrum and duodenum that takes place in the fundic repletion by food during trivial meals.

2. Background of the Invention

The body weight and the distribution of fat are regulated by a number of neurological, metabolic and hormonal mechanisms that keep a balance between the intake of nutrients and the consumption of energy.

When these control mechanisms of control are incorrectly regulated, thus leading to an excessive intake in relation to the consumption of energy, a surplus storage of energy takes place as fat, the result of which is an increase in the body weight. The obesity is, therefore, defined as an excess of the accumulation of fat in the body. When this accumulation rises to a great extent, it is then called morbid obesity.

The most objective and mostly used way doctors apply to quantify the obesity is the calculation of the Index of Body Mass or simply IMC, which index is obtained by dividing the weight in kilograms by the height in meters to the square ($IMC=P/A^2$). The regular weight considered for the IMC varies in the range from 19 to 25 $Kg/m^2$. People with IMC's from 25 to 30 are considered as over-weighted while those between 30 and 40 already are classified as obese. Finally, people with IMC's above 40 are those having morbid obesity, that is, equivalent to approximately 45 kg above the optimum weight. The stratification of the individuals based on the IMC by grouping them in different classes of weight maintains a direct relationship with the mortality rate, varying from "very low" in people within the regular range to "very high" in those having an IMC above 40 $kg/m^2$.

There are a number of therapeutical alternatives that, when combined, attain significant losses of weight, such as the diets concerned with low and very low calories, psycotherapy, behavior therapy, physical exercises, and some drugs that increment the therapeutical armory stock against obesity.

However, in the case of morbid obesity, most of the time such measures are ephemeral and inefficient. It is so in view of the fact that most of the severely obese patients are not able to promote a definitive change in their nourishing habits and when practicing physical activity, in connection with the changes in the mechanisms that control the distribution of fat and waste of energy, thus leading to a tendency of the individual to recover the weight he had lost, also surpassing the initial weight and becoming still more obese.

Therefore, the patients with a morbid obesity must be seen as bearers of a severe illness that threatens life, reduces the quality of life and self-esteem, and they require efficient approaches to promote a weight reduction definitively; therefore, to individuals with a severe obesity, some treatments, such as surgery and others related thereto are then considered to be scientifically proven methods that promote a fierce long-lasting weight reduction, thus reducing the mortality rate and solving, or at least minimizing, a number of illnesses related to the obesity.

One of the best known treatments for inducing the reduction of the body weight is comprised of the installation of an intra-gastric balloon, what has taken place for the first time in 1979, by Henning. In 1982, an intra-gastric device made of latex was reported by Nieben and Harboe. The use of a version manufactured in plastic produced by Garren-Edwards with a volume of 200 ml, gained ground in the USA after the approval by the USA FDA in 1985. However, controlled and retrospective pursuings have shown that the weigh reducing effect was ephemeral, reaching an apex three to six months after the implantation and accompanied by complications including gastric ulcers in 2.5% of the patients, gastric complaints that required the early removal of the balloon in 5% of the patients. The physicians have had problems with the implantation of the balloon and mechanical difficulties in the removal in 28.7% of the cases as reported by Frank, et al. in 1987.

Well-known studies have shown that the weigh reducing effect of these balloons was comparable to that of ghost balloons and diets connected with the induction of a change in the nourishing behavior by Benjamin, et al. and Meshkinpour, et al. in 1988. Next, balloons with higher volumes have been designed in the assumption that the intragastric volume more restricted to the input of food could be an efficient weight reduction inducing means.

A 550 ml pear-shaped version designed by Taylor propitiated the loss of 11.6% of the body weight and a decline of 11.4% of the IMC in 60 patients. In 2000, with 590 ml balloons, Bonassi, et al., showed that a 25 kg reduction can be attained in patients with an IMC higher that 40 in a period of up to four months if associated to a moderately restrictive diet, said reduction only being able to be partially maintained up to 12 months without the addition of other supportive measures. In patients with IMC's between 30 and 40, the weight reduction until the fourth month is lower (12 kg), however, it persists in the long-term period. Evans and Scott, in 2001, reported a 18.7% reduction of the surplus weight 4 to 7 months after the implantation, said reduction being 15 loss kg in 68 patients having IMC's above 40, and recommended the removal thereof between 3 and 6 months in order to prevent complications that they have deemed to be severe, such as intestinal occlusion at the ileum and sigmoid level that had required surgeries for changing the situation (3 chaos in 68). Such authors also reported the spontaneous elimination of the device through the rectum in 14 patients after up to 6 months of implantation.

It is clear, therefore, that these devices only function partially for a limited time. They are essentially indicated as means that induce the body weight reduction that precedes a "definitive" surgical treatment in patients having IMC's higher than 40. Apparently, the reduction is lower in those having IMC's between 30 and 40, though a long-term effect may be expected. It is evident that the physiological rules for the application thereof seem to be insufficient, too.

Studies in animals and human beings have shown that the post-prandial satiety is influenced by a multiplicity of factors. The gastric tonus, the intragastric contents and the counter-response to the stimulation of receptors located in the lower intestine would be the main factors among same. In animals, the gastric expansion is a well-known signal for the satiety. By using barostatic techniques in human beings, it is possible to prove the relationship between the tonus of the proximal stomach and the occurrence of gastrointestinal sensations that include the appetite.

In 1997, Jones, et al. demonstrated that the expansion of the gastric antrum is intimately associated with the post-prandial completeness in opposition to the expansion of the proximal stomach.

In 2002, Rao, et al. demonstrated that the expansion below the level of perception of the gastric bottom with balloons in human beings evokes a motor activity in the gastric antrum and duodenum, that is, there is a motor adaptation that compensates for the expansion of the gastric bottom and that would make the gastric depletion easier. As a result, the incorporation of energy through this route is inevitable under the conditions that mimic the fundic expansion which is the proposal of the large volume intra-gastric balloons.

From the above, it is clearly seen that the current knowledge of the gastroduodenal physiology allows for the proposal of a intra-gastric device that induces weight reduction by means of the expansion of the gastric antrum and that, by being stationary in the antrum, provides the antrum pyloric sub-occlusion only during the response to the increase in the motor activity of the antrum and the duodenum that occurs in the fundic repletion by food during trivial meals.

The present applicant has already filed a patent application for an intragastric balloon on Aug. 13, 2002 under n° PI 0203301-1, which discloses "improvements introduced for implants in cavitary bodies", basically comprising the implant of the type comprised of an ellipse-shaped silicone bag that is manufactured through the process that overlaps medical grade silicone layers duly approved by the FDA, thus forming a container for storing liquid or air; said implant being internally provided with a retention valve, while in the external face of said valve a solid medical grade silicone handle was provided, which handle remains rolled up inside the balloon and, after being drawn, it unwinds the wire where the light of the endoscope should pass through; said valve being provided with a solid silicone rod having a return memory that prevents the fluid to pass through as soon as the filling needle is pulled out; said filling needle being projected from the end of fluid passage rod, and said rod being provided with a three-way valve in the end opposite thereto.

BRIEF DESCRIPTION OF THE INVENTION

The intragastric balloon device semi-stationary in the antrum, called BSEAG herein-below, that induces the loss of the appetite and early prandial satiety, is comprised of a inflatable per-os silicone balloon which is biologically inert and compatible for medical use, with a volume of up to 240 ml to be filled with a non-elastic fluid provided with radio-opaque contrast and dye, preferably methylene blue that turns same into a pear-shaped or spherical balloon after it is filled up, which balloon is to be endoscopically placed in the distal stomach; said balloon is preferably provided with an inner valve having a solid silicone rod provided with a return memory that prevents the fluid from passing through as soon as the filling needle is pulled out.

Appended to the pyloric pole of said balloon, opposite to the cited valve, is a 35 to 45 cm silicone rod, called duodenal rod herein-below, preferably having 35 cm of length and a 5 mm diameter. Said rod is particularly located in the second portion of the duodenum and is provided in the distal end thereof with a metallic counterweight peristaltic-propellant whose calculated weight is of 7 g for the dimension cited above.

The function of thus described balloon BSEAG is the perennial expansion of the gastric antrum, whilst the function of the duodenal rod is the semi-stationary anchoring of the balloon in the distal stomach.

The presence of contrast in the filling fluid makes the radiological visualization of the location of the balloon in the gastrointestinal tract easier. The methylene blue dye, which is biologically harmless, is easily absorbed by the mucosa of the gastrointestinal tract and excreted by the kidneys in the urine. Therefore, the function of the methylene blue is to detect at once any eventual leak of the filling fluid from the balloon due to the appearance of a bluish coloration of the urine.

The implant will be placed by means of high digestive endoscopy under sedation. The duodenal rod will be guided as far as the second portion of the duodenum, in such a way that the balloon is provided with a self-contending valve in the port of the inflation catheter. This is provided with a system for the external release of the balloon after it is inflated.

OBJECT OF THE INVENTION

The pear-shaped or spherical balloon BSEAG, after the implantation, placed by means of endoscopy, expands the distal stomach permanently, thus inducing the early satiety in the prandial period and loss of appetite in the inter-prandial period below the perception level. The expansion of the bottom when food is received during the immediate prandial and post-prandial period induces an increase in the motor activity of the distal stomach and duodenum. This activity draws the balloon towards distal positions of the stomach as a function of the increase in the gastric peristalsis and the drag that the duodenal peristalsis will exert on the rod and counter-weight.

Next, the gastric exit route is partially occluded and prevents the full gastric emptiness. The antrum pyloric removal takes place next with the gastric retro-peristalsis and the antrum relaxation allowing the balloon to move towards the proximal direction. Small portions of the alimentary cake that are present in the antrum are then released in the duodenum in a relative gastric atony regimen and high sensation of completeness and satiety.

The advantages of the balloon BSEAG are consistent with the gastroduodenal mechanisms for inducing the early satiety and loss of appetite in opposition to the mere restrictive character of large volume balloons.

The perception of inter-prandial epigastric discomfort is considerably lower as a function of the lower volume of the balloon BSEAG.

The potential weight reducing efficiency of the BSEAG is higher because it has the unique characteristic of setting in motion a number of physiological issues of the gastroduodenal segment involved in the early satiety and the reduction of the appetite.

BRIEF DESCRIPTION OF THE DRAWINGS

To compliment the present description in order to get a better understanding of the characteristics of the present invention and according to a preferred practical embodiment thereof, a set of drawings is attached to the description, wherein, in an exemplified non-limiting way, the following is represented:

FIG. 1 illustrates schematically the stomach and the duodenum provided with the pear-shaped semi-stationary intra-gastric balloon in the antrum and the duodenal rod with the counter-weight;

FIG. 1A is a detailed cut view of the pear-shaped balloon;

FIG. 2 illustrates details of the distal end of the duodenal rod; and

FIG. 3 illustrates an expanded cut view of the distal end of the rod and counter-weight.

DETAILED DESCRIPTION OF THE INVENTION

With reference to the illustrated drawings, the present invention is related to a semi-stationary balloon in the gastric antrum provided with an anchoring rod for inducing weight reduction in human beings, an intragastric balloon device (1), called BSEAG herein-below, provided with an anchoring rod, called duodenal rod (2) herein-below, a means for inducing the reduction of appetite and early prandial satiety and particularly placed by means of endoscopy in a semi-stationary way in the gastric outlet, that is, in the gastric antrum (GAC) and in the duodenum (D).

The balloon BSEAG (1) comprises an inflatable per-os silicone balloon which is biologically inert and compatible for medical use with a volume of up to 240 ml, an average 120 ml volume to be filled with a non-elastic fluid provided with radio-opaque contrast and dye, preferably methylene blue that turns same into a pear-shaped or spherical balloon as soon as it is filled up, with a maximum volume of up to 240 ml and an average 120 ml volume, to be placed endoscopically in the stomach (E), particularly in the antrum (GAC); in said balloon, the inner face of the medium portion of lesser diameter of the pear-shaped form is coated with a malleable ribbon (f) that provides the balloon BSEAG with resistance and flexibility; said balloon being preferably provided with an inner valve (3) provided with a solid silicone rod having a return memory that prevents the fluid from passing through as soon as the filling needle is pulled out; said balloon can also adopt the spherical form preferably with a diameter measuring between 5.5 cm and 6 cm, said pear-shaped component having a length of up to 7 cm and a 3 cm lower pole maximum diameter, the optimum diameter being 2 cm and an upper diameter of 4 cm that can vary up to 6.

Attached to the pyloric pole (4) of the balloon BSEAG (1), opposite said valve (3) and welded thereto, is the flexible duodenal rod (2) integrally made of medical grade measuring between 45 cm and 35 cm, preferably with 35 cm of length and a 5 mm diameter.

In the distal end of said duodenal rod (2), a peristaltic propellant counter-weight (5) is disposed, which counter-weight comprises a silicone pipe (6) having a sealed distal end (6a), internally provided with portions of metallic conduits (7), the calculated full weight of which is 7 g for the dimension of the rod cited above. Said counter-weight (5) is particularly located in the second portion (a) of the duodenum.

The balloon BSEAG (1), after the implantation, expands the distal stomach permanently, thus inducing the early satiety in the prandial period and loss of appetite in the inter-prandial period below the perception level. The expansion of the bottom when the food is received during the immediate prandial and after-prandial period induces an increase in the motor activity of the distal stomach and the duodenum. This activity forces the balloon towards distal positions of the stomach as a function of the increase in the gastric peristalsis and the drag that the duodenal peristaltsis will exert on the connecting rod and counter-weight.

Next, the gastric outlet route is occluded and prevents the full gastric emptiness. The antrum pyloric clearing occurs next with the gastric retro-peristaltsis and the antral relaxation thus allowing the balloon to be moved towards the proximal direction. Small portions of the alimentary cake that are present in the antrum are then set free in the duodenum in a relative gastric atony regimen and high sensation of fullness and satiety.

It is important to understand that the description does not restrict its application to the details and steps described herein-above. The invention is susceptible to other embodiments and can be practiced or to realized in a variety of ways. It should be understood that the terminology used herein is for purposes of describing but not limiting the invention.

What is claimed is:

1. A semi-stationary balloon combination that is adapted to be placed in the gastric antrum for inducing weight reduction in human beings by inducing reduction of appetite and early prandial satiety, the balloon combination comprising: a flexible anchoring rod, an intragastric balloon connected to the flexible anchoring rod and adapted to be placed endoscopically in the stomach, the balloon being made of inflatable per-os medical grade silicone with a volume of up to 240 ml adapted to be filled with a non-elastic fluid provided with radio-opaque contrast and dye, the intragastric balloon being a pear-shaped form so that the balloon can be positioned in a semi-stationary way in the gastric antrum (AG); wherein, in said balloon, an inner face of a medium portion of lesser diameter of the pear-shaped form is coated with a malleable ribbon (F); said flexible anchoring rod (2) having a distal counter-weight (5) designed to be installed in a portion of the duodenum (D).

2. The combination of claim 1 wherein the flexible anchoring rod is made of medical grade silicone, wherein said rod is characterized in that it is appended and welded to a pyloric pole (4) of the balloon (1).

3. The combination of claim 1, characterized in that the rod (2) is made in a solid form with a length between 35 and 45 cm, and a 5 mm diameter.

4. The combination of claim 3, characterized in that the counter-weight (5) is comprised of a pipe (6) having a closed distal end (6a) being internally provided with metallic conduits (7).

5. The combination of claim 4, characterized in that the counter-weight (5) has a full weight of 7 g.

6. The combination of claim 1, characterized in that the counter-weight (5) is adapted to be located in the second portion of the duodenum.

7. The combination of claim 1, including a valve in the intragastric balloon.

8. A semi-stationary balloon combination that is adapted to be placed in the gastric antrum for inducing weight reduction in human beings by inducing reduction of appetite and early prandial satiety, the balloon combination comprising: a flexible anchoring rod, an intragastric balloon connected to the flexible anchoring rod and adapted to be placed endoscopically in the stomach, the balloon being made of inflatable per-os medical grade silicone with a volume of up to 240 ml adapted to be filled with a non-elastic fluid provided with radio-opaque contrast and dye, the intragastric balloon being spherical so that the balloon can be positioned in a semi-stationary way in the gastric antrum: said flexible anchoring rod having a distal counter-weight designed to be installed in a portion of the duodenum, the balloon having a diameter between 5.5 cm and 6 cm.

9. The combination of claim 8, including a valve in the intragastric balloon.

* * * * *